United States Patent [19]
Kahl et al.

[11] Patent Number: 5,487,312
[45] Date of Patent: Jan. 30, 1996

[54] GAS ANALYZER WITH REGULATED MEASUREMENT GAS FEED AND DYNAMIC DILUTION OF SAMPLES

[75] Inventors: Melchior Kahl, Bergisch-Gladbach; Friedhelm Risse, Köln, both of Germany

[73] Assignee: Mannesmann Aktiengesellschaft, Dusseldorf, Germany

[21] Appl. No.: 320,051

[22] Filed: Oct. 7, 1994

[30] Foreign Application Priority Data

Oct. 8, 1993 [DE] Germany .................. 43 34 336.8

[51] Int. Cl.$^6$ .................................. G01N 27/50
[52] U.S. Cl. .................... 73/863.01; 137/93; 137/893
[58] Field of Search .................... 73/23.2, 23.21, 73/863.01, 1 G; 137/93, 888, 893, 892; 422/98

[56] References Cited

U.S. PATENT DOCUMENTS

| | | | |
|---|---|---|---|
| 3,870,065 | 3/1975 | Minns, Jr. | 137/93 |
| 3,975,947 | 8/1976 | Kruishoop | 73/28.01 |

*Primary Examiner*—R. Raevis
*Attorney, Agent, or Firm*—Cohen, Pontani, Lieberman & Pavane

[57] ABSTRACT

A choke-bypass system is arranged upstream of the gas analyzer so as to generate a constant input pressure at the gas analyzer. The measurement range of the gas analyzer can be expanded considerably beyond the standard range while maintaining accuracy of measurement when the measurement gas is diluted with an inert gas above a given gas concentration threshold in such a way that the gas concentration in the gas analyzer remains constant. To this end, a dilution gas line (12) with a control valve (13) for continuous dilution of the measurement gas with the inert gas is connected to the choke-bypass system (1), (2), (3), (6). Further, the detector (3) of the gas analyzer is connected on the output side via a computer (10) with a dilution regulator (15) which readjusts the flow of inert gas via the control valve (13) in such a way that the amplified detector output signal is maintained at a given reference value, wherein the measurement gas flow is increasingly diluted as the measurement gas concentration increases. The dilution is then measured by a flow meter (14) arranged in the dilution gas line (12) and this measurement signal is processed together with the detector signal in a computer (10) connected with the detector (13) and dilution regulator (15) to form the analysis measurement.

6 Claims, 5 Drawing Sheets

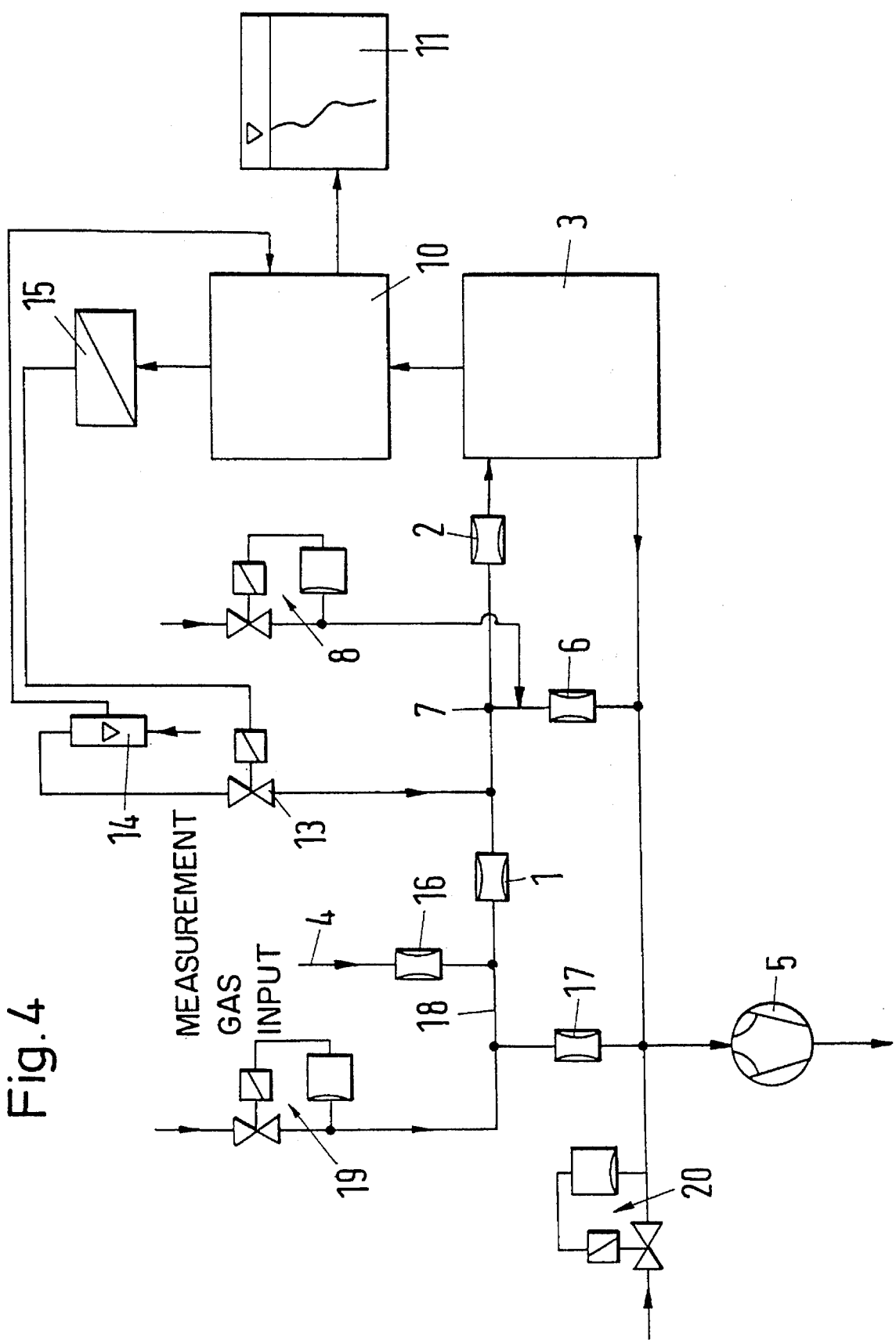

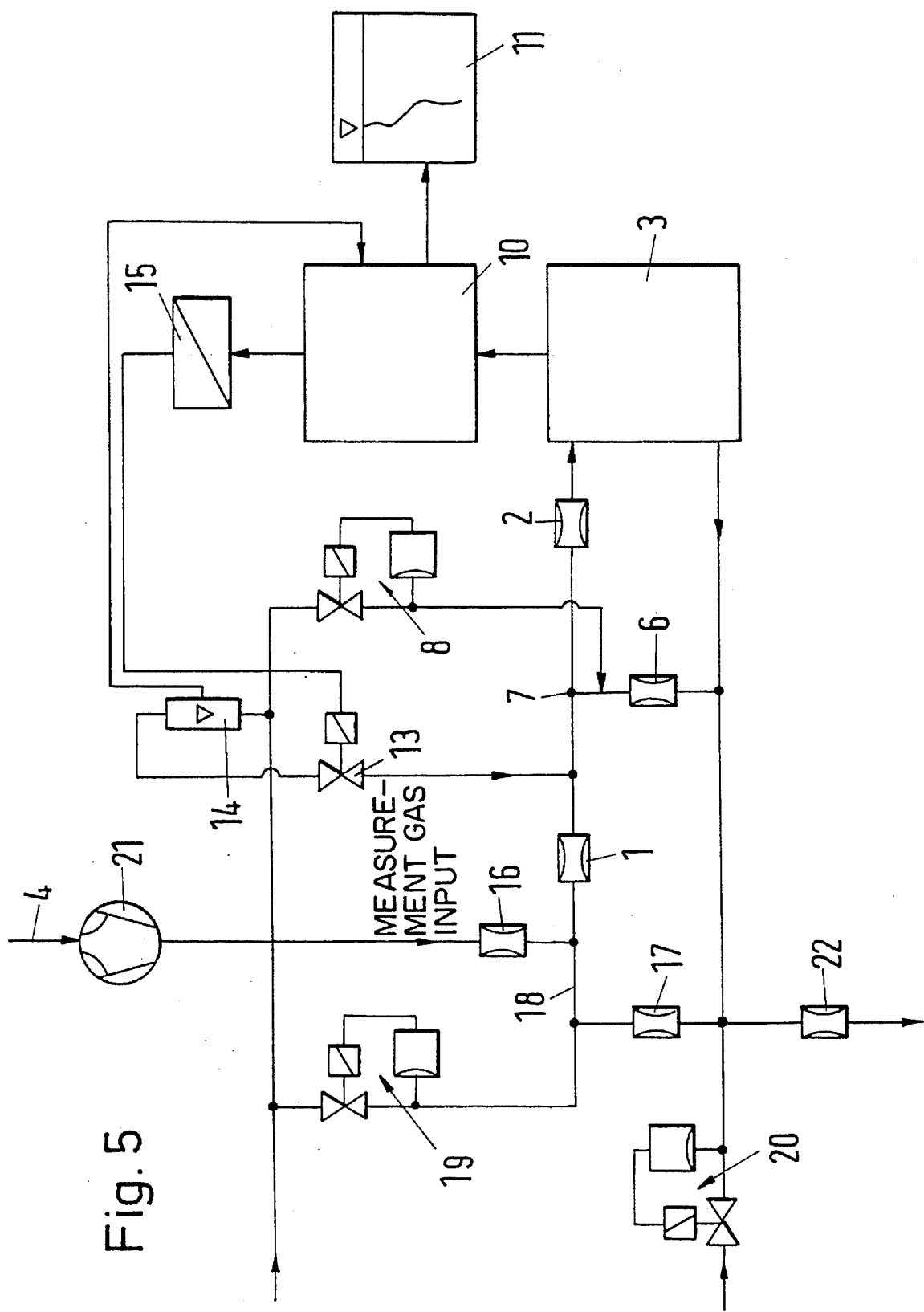

GAS ANALYZER WITH REGULATED MEASUREMENT GAS FEED AND DYNAMIC DILUTION OF SAMPLES

BACKGROUND OF THE INVENTION

The invention is directed to a continuously operating gas analyzer with a detector which is connected to a measurement amplifier and with regulated measurement gas feed. The measurement gas feed includes a measurement gas pump at the detector input or detector output, a first choke which is connected in the measurement gas line upstream of the detector, a second choke which is connected in parallel with the series connection of the first choke and detector as a bypass, a third choke which is arranged in the measurement gas line and connected in series upstream of the branch point of the lines leading to the first and second chokes, and a pressure regulator which maintains constant pressure at the common connection point of the three chokes. A measurement gas regulating arrangement of this type is described in DE 2 932 436.

Gas analyzers for measuring the concentration of a gas component are generally limited to a determined range of concentration, since the response curve outside this concentration range is not linear or, e.g., passes into saturation. This concentration range determines a so-called standard measurement range within which operation is normally effected. Many steps are known for expanding this measurement range or for detecting gas concentrations lying outside the standard measurement range with sufficient accuracy. In UV/VIS or IR spectroscopy, for example, the length of the cell can be decreased to reduce the optical path length. Further, it is known to dilute a very highly concentrated measurement gas flow in a defined manner.

U.S. PAT. NO. 3,975,947 describes a control loop by which concentrations of a substance in a sample flow can be determined in a continuous manner. The detector signal regulates a dilution flow in such a way that the signal assumes a constant value which corresponds in turn to a predetermined reference value. In order to maintain this reference value, the substance to be measured must be fed into the measurement gas flow upstream of the detector in the event that the sample flow does not contain this substance. The concentration to be determined can then be derived directly from the control variable of the regulator. The aim of the process is a constant calibration of the detector during measurement.

EP 71 132 describes a gas analyzer in which a flushing or scavenging gas which is free of measurement gas can be delivered to a cavity upstream of the sensor by means of a pump. The sensor is connected with a measurement amplifier arranged downstream together with the pump as a control loop which switches on the pump when the sensor signal reaches a threshold value and increases the output of the pump as the sensor signal increases. An overloading of the electrochemical sensor due to excessively high gas concentrations can be prevented by these steps. In principle, a given standard measurement range can also be expanded in the same manner. The present invention is based on this idea.

SUMMARY OF THE INVENTION

The invention has the object of expanding the standard measurement range in a continuously operating gas analyzer with regulated measurement gas feed in such a way that increased measuring accuracy can be achieved throughout the expanded measurement range. This demand cannot be satisfied by the measuring device described in EP 71 132.

Proceeding from the continuously operating gas analyzer with a choke-bypass system arranged upstream, this object is met according to the invention in that a) a dilution gas line with a control valve for continuous dilution of the measurement gas with an inert gas is connected to the measurement gas line between the first and third chokes;

b) the detector is connected at the output side via a computer with a dilution regulator which readjusts the inert gas flow via the control valve in such a way that the amplified detector output signal is maintained at a given reference value, the dilution of the measurement gas flow increasing as the measurement gas concentration increases; and c) a flow meter is arranged in the dilution gas line, the measurement signal of this flow meter being processed together with the detector signal in a computer connected with the detector and dilution regulator to generate the analysis measurement.

The dilution of the measurement gas is preferably first regulated when the measurement amplifier signal has exceeded a given threshold value lying within the standard measurement range.

The cross section of the chokes connected upstream of the detector is advisably dimensioned in such a way that the control valve of the pressure regulator at the detector input is virtually completely open when the control valve in the insert gas line is virtually completely closed. A particularly great expansion of the measurement range can be achieved by this step.

In order for the gas analyzer to operate independently from the input pressure within a certain range, the choke connection is advantageously modified in such a way that a fourth choke is arranged in the measurement gas line upstream of the third choke and an additional bypass line with a fifth choke leads from the connection point of these two chokes directly to the detector output. At the same time, an additional pressure regulator connected to the connection point ensures that the pressure remains constant.

Another improvement consists in that a pressure regulator is also installed at the detector output so as to maintain constant pressure at the detector output. The dependence of the gas analyzer on pressure and mass flow can be compensated for by this additional pressure regulating arrangement at the output.

Alternatively, these same requirements can be met in that the measurement gas pump is arranged upstream of the analyzer as a pressure pump and in that a sixth choke is connected in series downstream of the detector output.

The invention achieves the following advantages:

The measurement range can easily be expanded beyond the standard measurement range by a factor greater than 10 with the same level of measuring accuracy throughout the entire expanded measurement range.

The additional cost on apparatus for the expanded measurement range is relatively small.

Combustible gases, e.g., gases of zone 0, can also be measured easily by selecting a relative low threshold value for the start of the regulated measurement gas dilution.

The useful life of the gas analyzer can be increased (low contamination) as a result of diluting the measurement gas.

In the following, embodiment examples of the invention are described more fully with reference to drawings.

BRIEF DESCRIPTION OF THE DRAWINGS

FIGS. 2 to 5 show block diagrams for different constructions of the gas analyzer with regulated measurement gas feed and dynamic measurement gas dilution.

DETAILED DESCRIPTION OF THE PREFERRED EMBODIMENTS

Figure 1:
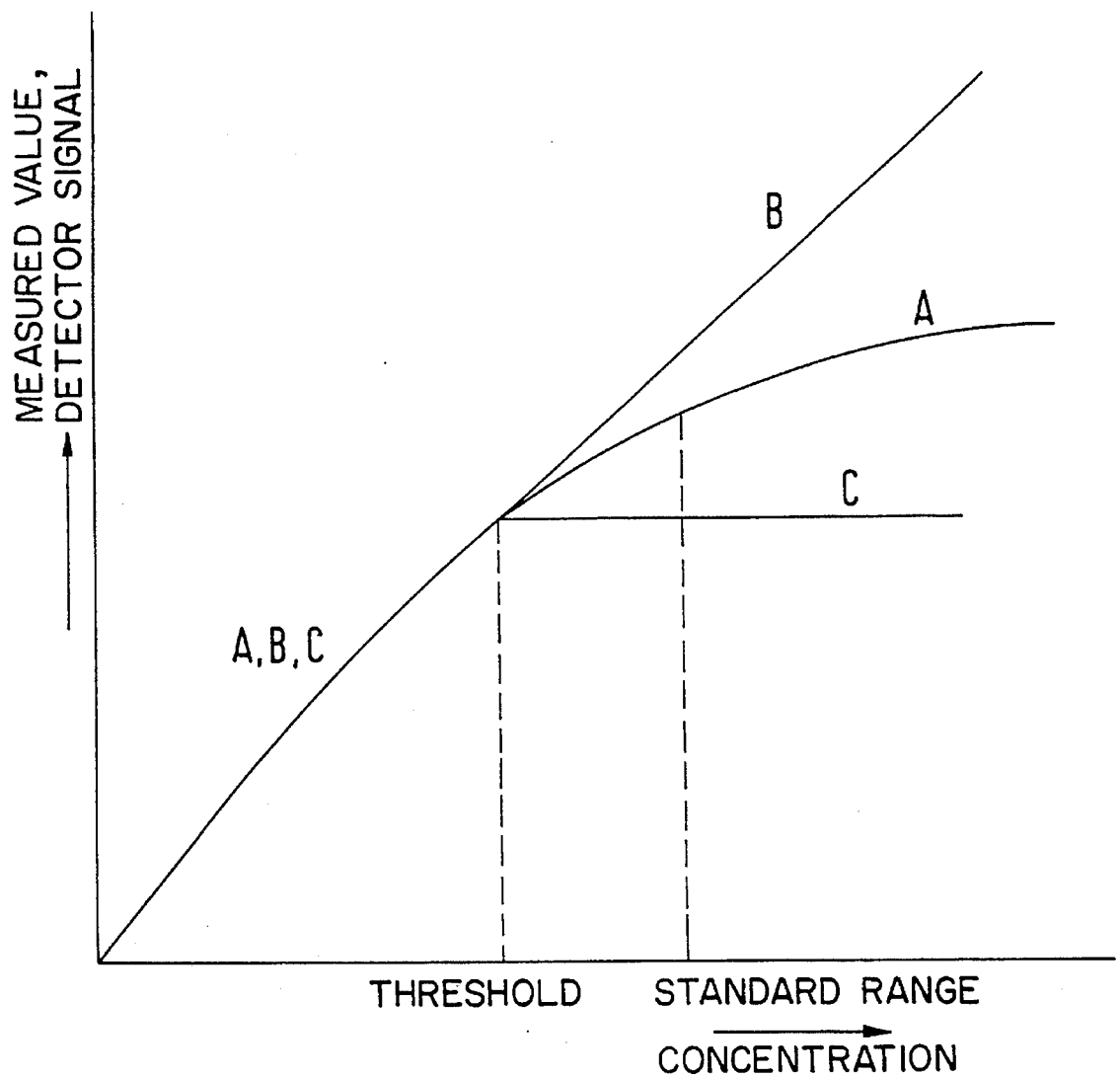
FIG. 1 shows a typical calibration curve of an electrochemical sensor without dynamic gas dilution (A) and with dynamic gas dilution (B)

With reference to FIG. 1, the measurement principle with dynamic dilution of samples will be explained first. In the diagram shown in FIG. 1, the measured detector output signal or analysis measurement of an electrochemical sensor is plotted as a function of the concentration of partial pressure of the analyzed gas components. In the normal case, a curve is obtained which approaches saturation at high concentrations (curve A). In this case, the measured value corresponds to the detector output signal. In a calibration curve of this kind, the standard measurement range is defined as that concentration range which can still be detected by the detector with a desired given measuring accuracy. If this measurement range is exceeded, the measurement errors due to the slight increase in the calibration curve are too great.

The measurement range can be expanded considerably beyond the standard range while maintaining accuracy of measurement when the measurement gas is diluted with an inert gas above a given gas concentration threshold in such a way that the gas concentration remains constant at the detector of the gas analyzer. To this end, the detector output signal is fed to a control loop which ensures that the measurement gas is diluted to an increasing extent as the concentration increases above said threshold concentration. Thus, the detector is acted upon by a constant measurement gas concentration above the threshold concentration. Consequently, the detector output signal also remains constant above the threshold value (curve C in FIG. 1). The analysis measurement above the threshold concentration is then given by the dilution necessary to maintain a constant gas concentration at the detector. For this purpose, the dilution is measured by a flow meter. According to FIG. 1, the measured values above the threshold concentration lie on a straight line B which forms a tangent to the calibration curve at the point of the threshold concentration. The threshold for the start of dilution is preferably set at a value between 60% and 90% of the maximum concentration of the standard measurement range. In principle, however, the selected threshold value may also be as small as desired so that dynamic dilution of measurement gas is used practically within the entire range of the calibration curve. An example for the formation of the analysis measurement as a function of the measured dilution is described below.

Figure 2:
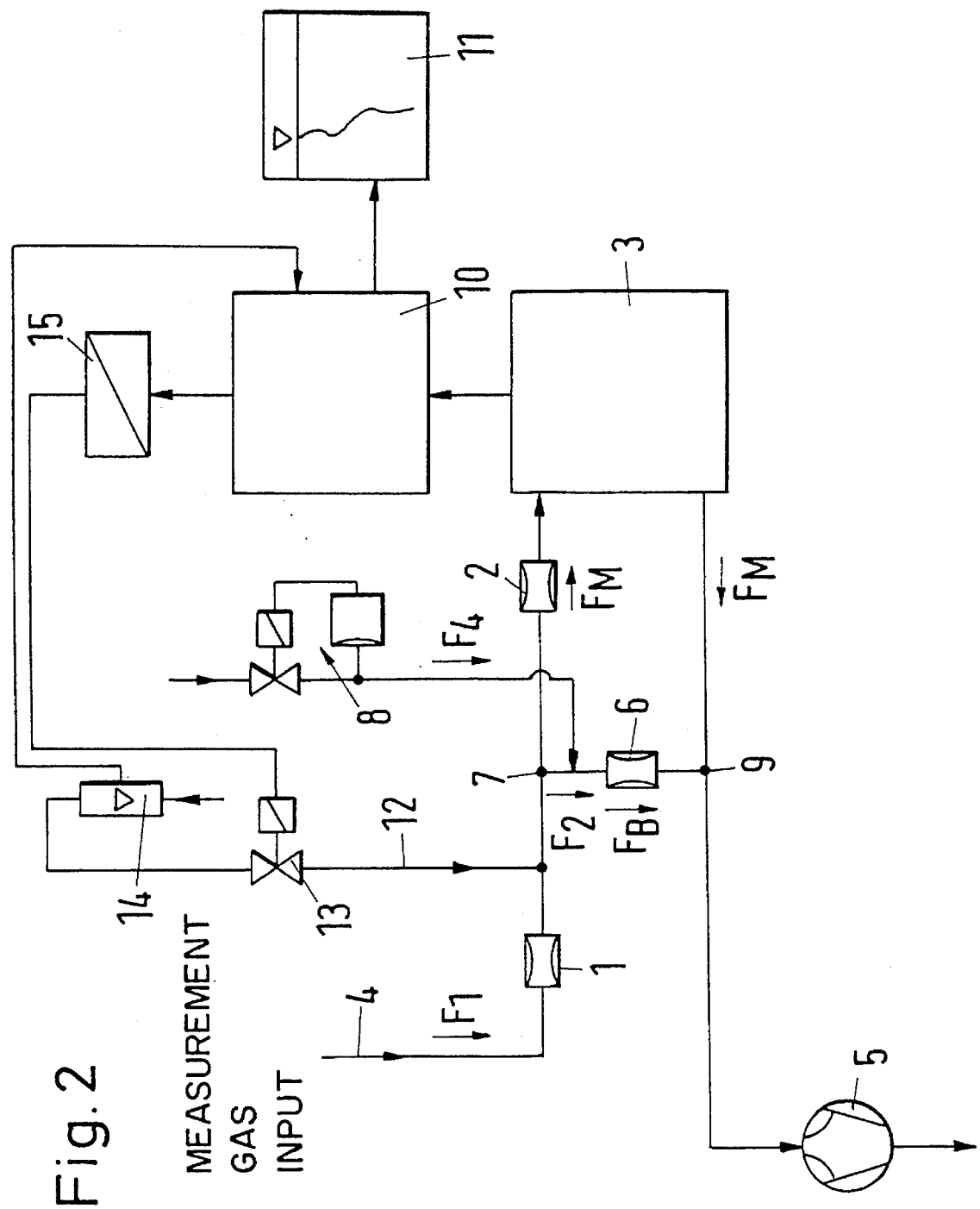

An embodiment example for the simplest form of a measuring and control loop for dynamic dilution of samples is shown in FIG. 2. The measurement gas to be analyzed under input pressure $P_1$ is fed to the detector 3 via a series connection of two fixed chokes 1 and 2 (third and first chokes). The detector 3 can be, e.g., an electrochemical sensor, a spectrometer, photometer or a flame ionization detector. Choke 1 is connected with the measurement gas input 4 and choke 2 is connected with the detector 3. The output of the detector 3 is connected to a suction pump 5 so that the detector output is brought to a pressure well below atmospheric pressure. An additional choke 6 (second choke) is connected in parallel with the series connection of the first choke 2 and detector 3 as a bypass. The third choke 1 is connected in series upstream of the branch point 7 of the lines leading to the first choke 2 and second choke 6. A pressure regulator 8 which maintains constant pressure $P_2$ at branch point 7 is connected to the line between chokes 1 and 2. Thus, branch point 7 is the common connection point of the three chokes 1, 2 and 6, while the line with choke 6 forms a bypass which is connected in parallel with the series connection of detector 3 and choke 2. The measurement gas flow $F_1$ divides into two partial flows at branch point 7. One portion $F_M$ flows through the detector 3, while the other portion $F_2$ combines with the air flow $F_4$ sucked in through the negative pressure regulator 8. The two partial flows $F_2+F_4$ form the bypass flow $F_B$ which combines at junction 9 with the partial flow $F_M$ coming from the detector 3. The sum of these partial flows is sucked out through the suction pump 5. The detector signal depending on the gas concentration is amplified (measurement amplifier) and fed to a computer 10 for processing the measured value. The analysis measurement is recorded by a recorder or plotter 11.

A dilution line 12 communicating with the atmosphere via a control valve 13 and a flow meter 14 is connected to the connection line between chokes 1 and 2. As will be described in the following, an inert gas, e.g., atmospheric oxygen, which is regulated with respect to flow is fed through the dilution line 12 to dilute the measurement gas sample. The dilution of the measurement gas first starts when a limiting value of the detector signal which corresponds to a given threshold concentration and is stored in the computer 10 is exceeded. The control valve 13 which is actuated by an electric motor is connected with a dilution regulator 15 which is connected with the computer 10. The computer 10 sets the above-mentioned threshold value as a reference value for the dilution regulator 15. When there is a further increase in the measurement gas concentration, the regulator 15 ensures that sufficient dilution gas is proportioned to the measurement gas so that the concentration of measurement gas flowing to the detector 3 remains constant. The signal generated by the flow meter 14 is used in forming the analysis measurement above the threshold concentration. This signal is fed to the computer 10 for processing the measured value. In the dilution control loop which is formed by the regulator 15 of the control valve 13, the measurement unit (detector) 3 and the computer 10, the measurement signal coming from the detector 3 is the controlled quantity or manipulated variable and the dilution gas flow is the control variable.

In dimensioning the chokes 1, 2 and 6, the following points must be taken into account:

1. The flow resistance of choke 1 is selected so as to produce a sufficiently high sum of measurement gas flow $F_M$ and bypass flow $F_B$ at the lowest occurring measurement gas input pressure.
2. The flow resistance of choke 2 is selected in such a way that the measurement gas flow $F_M$ is still sufficiently great.
3. The bypass choke 6 is dimensioned in such a way that a bypass flow $F_B$ is generated whose flow quantity is at least twice that of the partial flow $F_2$ flowing from branch point 7 into the bypass.
4. Chokes 1, 2 and 6 are adapted to one another with respect to cross section in such a way that the control valve belonging to the pressure regulator 8 is virtually completely open when the control valve 13 in the inert gas line 12 is virtually completely closed.

The regulated measurement gas feed by means of the choke system 1, 2 and 6 is dependent on the pressure at the measurement gas input 4 and is only suitable for detectors which are not dependent on the mass flow If the detector supplies a pressure-dependent measurement signal, constant pressure ratios must be ensured at the detector unit or the pressure must be measured in the detector unit and the measured value must be appropriately adjusted.

Figure 3:
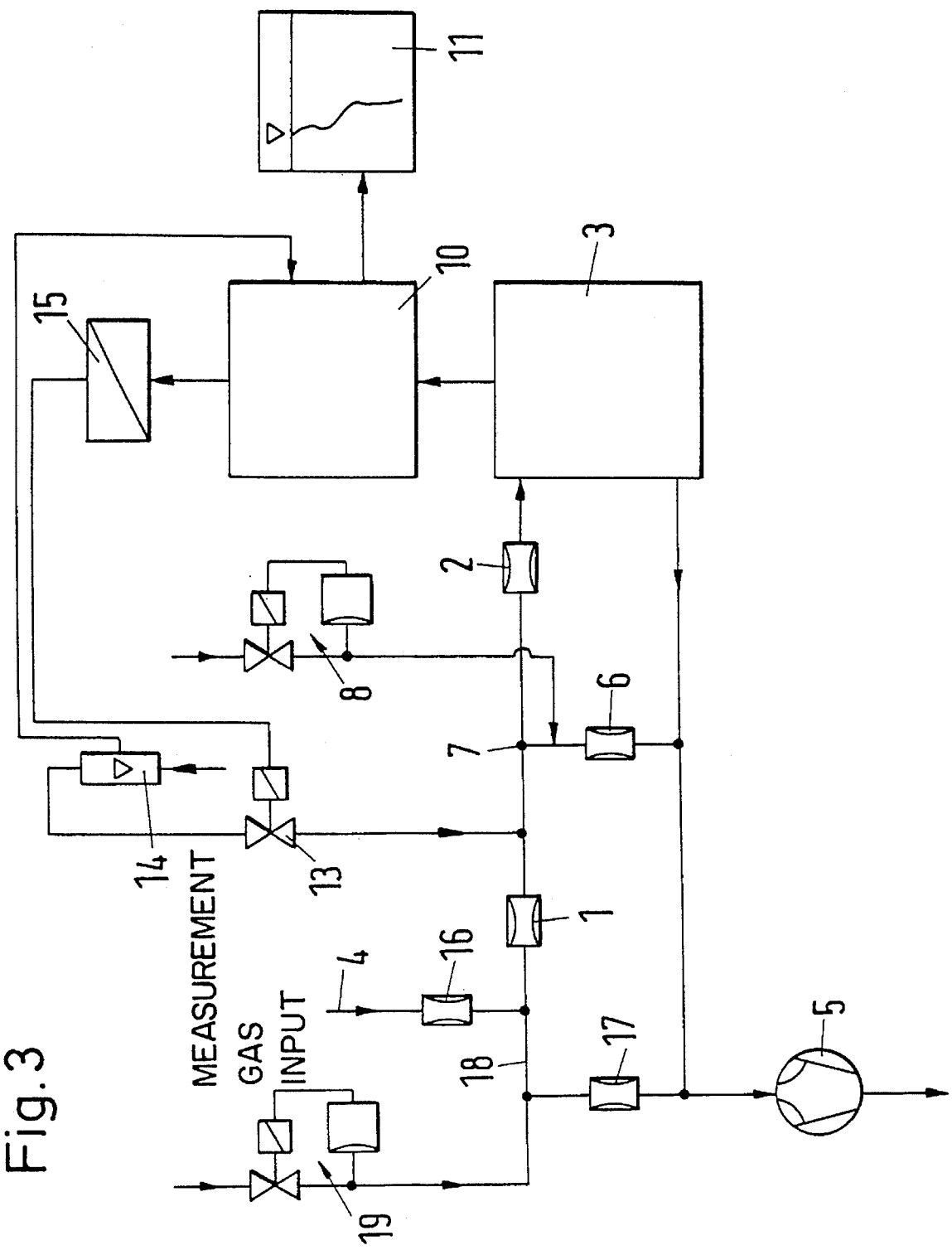

If the device according to FIG. 2 is supplemented, as shown in FIG. 3, by a choke 16 which is connected in series upstream of the measurement gas input and by an additional bypass choke 17 as well as another pressure regulator 19 which is connected to the connection point 18 of chokes 16 and 17, the measuring apparatus is substantially independent of the input pressure. A constant pressure is generated upstream of choke 1 so that the flow of gas through choke 1 remains constant. The measuring accuracy within the range of the dynamic dilution of measurement gas (curve portion B in FIG. 1) can accordingly be substantially improved. However, the dependence on pressure and mass flow specific to the detector persists.

This dependence on pressure and mass flow can be eliminated by means of an additional negative pressure regulator 20 at the detector output which is connected between the detector 3 and the pump 5, since the detector output pressure is maintained constant. This construction is shown in FIG. 4.

A common feature of the devices shown in FIGS. 2 to 4 consists in that the measurement gas is sucked in at input 4. Alternatively, it is also possible to use a pressure pump (compressor) 21 at the detector input rather than a suction pump 5 at the detector output for the regulated feed of measurement gas to the detector 3 so that the pressure prevailing at the pressure regulators 8 and 19 at the input side is higher than the pressure at detector 3. Moreover, in this alternative form shown in FIG. 5, an additional choke 22 is provided at the detector output, the pressure regulator 20 being connected to the connection point of the latter with detector 3. In the devices according to FIGS. 3 to 5, the dynamic dilution of measurement gas by means of the regulator 15 of the control valve 13 is analogous to the control loop according to FIG. 2.

In the following, the formation of the analysis measurement in the dynamic dilution of samples, i.e., in gas concentrations above the threshold concentration (see FIG. 1), is explained. The measured value is calculated in the computer 10 (measured value algorithm) by the following formula:

$$c_x = c\left(1 + \frac{Q_2}{Q_1}\right),$$

where $c$ is the concentration of measurement gas at detector 3, $Q_1$ is the volume flow of the measurement gas at choke 1 at the measurement gas input, and $Q_2$ is the volume flow of the dilution gas (inert gas).

The volume flow of the inert gas is measured by the flow meter 14. Volume flow $Q_1$ can be determined by calibration in which the detector output signal is measured with a measurement gas at a given concentration. This concentration should not exceed the threshold concentration. Subsequently, the control valve 13 in the dilution gas line 12 is opened until the detector signal is only half as large. In this case, the volume flow measured by the flow meter 14 equals volume flow $Q_1$. This assumes a linear dependence of the detector signal on concentration. If the relationship between the detector signal and concentration is logarithmic, for example, a suitable conversion must be carried out. In order to determine volume flow $Q_1$ more precisely, a series of measurements can be taken with different dilutions and the results can then be averaged. The analysis measurement formed according to the measured value algorithm mentioned above is sent by the computer 10 to the output unit, e.g. a plotter 11, and displayed.

We claim:

1. A continuously operating gas analyzer, comprising: a detector having an input and an output; a regulated measurement gas feed including a measurement gas pump (5, 21) at the detector input or detector output, a first choke (2) which is connected in a measurement gas line upstream of the detector (3), a second choke (6) which is connected in parallel with the series connection of the first choke (2) and the detector (3) as a bypass, a third choke (1) which is arranged in the measurement gas line and connected in series upstream of a junction (7) of the first choke (2) and the second choke (6), and a pressure regulator (8, 25) which maintains constant pressure at the junction (7) of the three chokes (1, 2, 6);

a dilution gas line (12) with a control valve (13) for continuous dilution of the measurement gas with an inert gas, the dilution gas line being connected to the measurement gas line between the first choke (2) and third choke (1);

a dilution regulator (15) connected to the output of the detector via a computer (10) which dilution regulator is operative to readjust the inert gas flow via the control valve (13) in such a way that an amplified detector output signal is maintained at a given reference value, wherein the dilution of the measurement gas flow increases as the measurement gas concentration increases; and a flow meter (14) arranged in the dilution gas line (12), the flow meter (14) having a measurement signal that is processed together with the detector signal in the computer (10) connected with the detector (3) and dilution regulator (15) to generate the analysis measurement.

2. A gas analyzer according to claim 1, wherein regulation of the dilution of the measurement gas first starts when the amplified detector signal has exceeded a given threshold value lying within the standard measurement range.

3. A gas analyzer according to claim 1, wherein the pressure regulator includes a control valve, the chokes (1, 2, 6) connected upstream of the detector (3) being dimensioned in such a way that the control valve of the pressure regulator (8, 25) at the detector input is virtually completely open when the control valve (13) in the dilution gas line (12) is virtually completely closed.

4. A gas analyzer according to claim 1, and further comprising a fourth choke (16) arranged in the measurement gas line upstream of the third choke (1) and an additional bypass line with a fifth choke (17) leads from a connection point (18) of the fourth and fifth chokes directly to the detector output, and still further comprising an additional pressure regulator (19, 24) that maintains the pressure at this connection point (18) constant.

5. A gas analyzer according to claim 4, and further comprising an additional pressure regulator (20, 23) provided at the detector output so as to maintain constant pressure at the detector output.

6. A gas analyzer according to claim 4, wherein the measurement gas pump is at the detector input and is a pressure pump (21), and further comprising a sixth choke (22) connected in series downstream of the detector output.

* * * * *